(12) United States Patent
Zabudkin et al.

(10) Patent No.: US 10,030,043 B2
(45) Date of Patent: Jul. 24, 2018

(54) METHOD FOR THE SYNTHESIS OF CLOFARABINE

(71) Applicant: Synbias Pharma AG, Schaffhausen (CH)

(72) Inventors: Alexander Zabudkin, Gerusbach (DE); Victor Matvienko, Mannheim (DE); Iaroslav Matviienko, Mannheim (DE); Volodymyr Sypchenko, Mannheim (DE)

(73) Assignee: Synbias Pharma AG, Schaffhausen (CH)

( * ) Notice: Subject to any disclaimer, the term of this patent is extended or adjusted under 35 U.S.C. 154(b) by 13 days.

(21) Appl. No.: 15/306,265

(22) PCT Filed: Apr. 22, 2015

(86) PCT No.: PCT/EP2015/058713
§ 371 (c)(1),
(2) Date: Oct. 24, 2016

(87) PCT Pub. No.: WO2015/162175
PCT Pub. Date: Oct. 29, 2015

(65) Prior Publication Data
US 2017/0044204 A1    Feb. 16, 2017

(30) Foreign Application Priority Data
Apr. 23, 2014 (EP) .................................... 14165627

(51) Int. Cl.
*C12P 19/40* (2006.01)
*C12P 17/18* (2006.01)
*C07H 19/16* (2006.01)

(52) U.S. Cl.
CPC .............. *C07H 19/16* (2013.01); *C12P 19/40* (2013.01); *C12Y 204/02001* (2013.01)

(58) Field of Classification Search
CPC .................................. C12P 17/18; C12P 19/40
See application file for complete search history.

(56) References Cited

FOREIGN PATENT DOCUMENTS

| EP | 417999 | * | 3/1991 | .......... C07H 19/173 |
|---|---|---|---|---|
| EP | 2404926 A1 | | 1/2012 | |
| WO | 2014177585 A2 | | 11/2014 | |
| WO | 2014177585 A3 | | 1/2015 | |

OTHER PUBLICATIONS

Bauta, William E., et al.: "A New Process for Antineoplastic Agent Clofarabine", Organic Process Research & Development, vol. 8, No. 6, Nov. 1, 2004, pp. 889-896.
Bonate, Peter L. et al.: "Discovery and development of clorafabine: a nucleoside analogue for treating cancer", Nature Reviews. Drug Discovery, Nature Publishing Group, vol. 5, No. 10, Oct. 1, 2006, pp. 855-863.
Burns, Charlene L., et al.: "Novel 6-alkoxypurine 2',3'-dideoxynucleosides as inhibitors of the cytopathic effect of the human immunodeficiency virus", Journal of Medicinal Chemistry, vol. 36, No. 3, Feb. 1, 1993, pp. 378-384.
Fateev, Ilja V., et al.: "The chemoenzymatic synthesis of clofarabine and related 2'-deoxyfluoroarabinosyl nucleosides: the electronic and stereochemical factors determining substrate recognition by E. coli nucleoside phosphorylases", Beilstein Journal of Organic Chemistry, vol. 10, Jul. 22, 2014, pp. 1657-1669.
International Search Report in International Application No. PCT/EP2015/058713, dated Jul. 7, 2015, 5 pages.
Taran et al., Enzymatic Transglycosylation of Natural and Modified Nucleosides by Immobilized Thermostable Nucleoside Phosphorylases from Geobacillus stearothermophilus. Russian Journal of Bioorganic Chemistry. 2009;35 (6):739-745.

* cited by examiner

*Primary Examiner* — Bruck Kifle
(74) *Attorney, Agent, or Firm* — McCarter & English, LLP; Steven G. Davis; Wei Song (57) ABSTRACT

The present invention relates to a method for the high yield production of the anticancer nucleoside clofarabine, the method comprising the preparation of 2-chloroadenosine by enzymatic transglycosylation between 2-chloroadenine and nucleosides, benzoylation, isomerization, sulfonate ester formation, fluorination, and deprotection.

8 Claims, 5 Drawing Sheets

METHOD FOR THE SYNTHESIS OF CLOFARABINE

This application is a U.S. National Stage Application of PCT/EP2015/058713 filed Apr. 22, 2015, which claims priority to European Patent Application No. 14165627.2 filed Apr. 23, 2014. The entire contents of the above-identified applications are hereby incorporated by reference in their entireties.

FIELD OF THE INVENTION

The present invention is directed to a method for the production of clofarabine in high yield and without formation of undesired α-N9 stereoisomers.

BACKGROUND OF THE INVENTION

Clofarabine (systematic IUPAC name: 5-(6-amino-2-chloro-purin-9-yl)-4-fluoro-2-(hydroxyl-methyl)oxolan-3-ol) is a purine nucleotide antimetabolite used for the treatment of various types of leukemias, in particular acute lymphoblastic leukemia.

Several methods for the production of clofarabine are currently established in the art. The synthesis routes are typically based on a coupling reaction between the purine derivatives and an arabinofuranosyl fragment. Depending on the method of fluorine atom introduction, these synthesis schemes can be divided into two groups: (i) methods in which a fluorine atom is included in a ribofuranose fragment and introduced in the molecule at the coupling step; (ii) methods in which a fluorine atom is introduced after the coupling step by chemical transformations of the nucleoside obtained previously.

Figure 1:
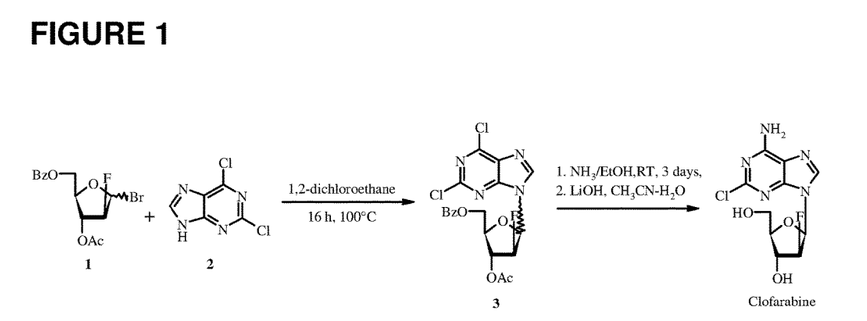
FIG. 1 illustrates the synthesis scheme for the production of clofarabine as disclosed in U.S. Pat. No. 5,034,518.

U.S. Pat. No. 5,034,518 discloses the original synthesis scheme for producing clofarabine developed by Montgomery and coworkers. The synthesis route is illustrated in FIG. 1. In brief, a 1-bromo-2-fluoro-sugar 1 is coupled with 2,6-dichloropurine 2, followed by the amination and deprotection steps. This coupling step results in formation of a mixture of α- and β-anomers of product 3. After chromatographic separation, it is possible to isolate the desired β-anomer with a yield of only 32%. The major disadvantages of this method are in fact the low overall yield of the desired product (13% based on 1), a low stability of starting bromide 1 and a challenging purification of coupling reaction product 3 due to the presence of α-isomer.

Figure 2:
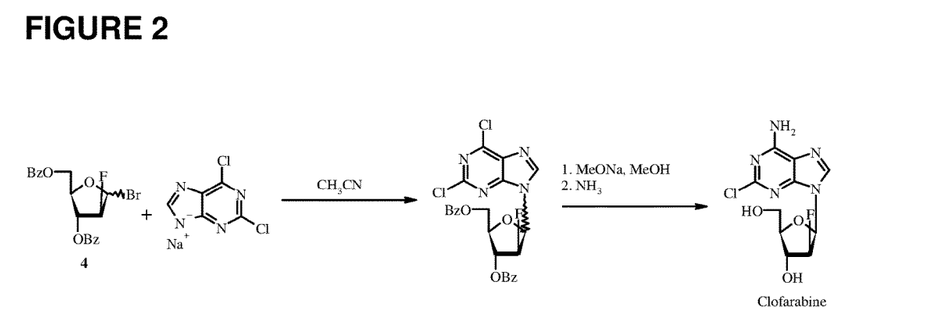
FIG. 2 illustrates the synthesis scheme for the production of clofarabine as disclosed in U.S. Pat. No. 6,949,640.

U.S. Pat. No. 6,949,640 discloses a modification of the above synthesis route involving (i) the use of salts formed by treatment of 2-chloro-6-substituted-purine with strong bases (such as NaH) instead of the NH-forms of purines, and (ii) the use of 2-deoxy-2-fluoro-3,5-di-O-benzoyl-α-D-arabinofuranosyl bromide 4 instead of O-acetyl derivative 1 (this synthesis pathway is illustrated in FIG. 2). These modifications made it possible to increase the total yield of clofarabine to about 40% based on compound 4. However, the synthesis scheme is hampered by the low stability of bromide 4, which is difficult to produce, and the formation of mixture of anomers at the coupling stage, requiring challenging column chromatography for the separation of the desired product.

Figure 3:
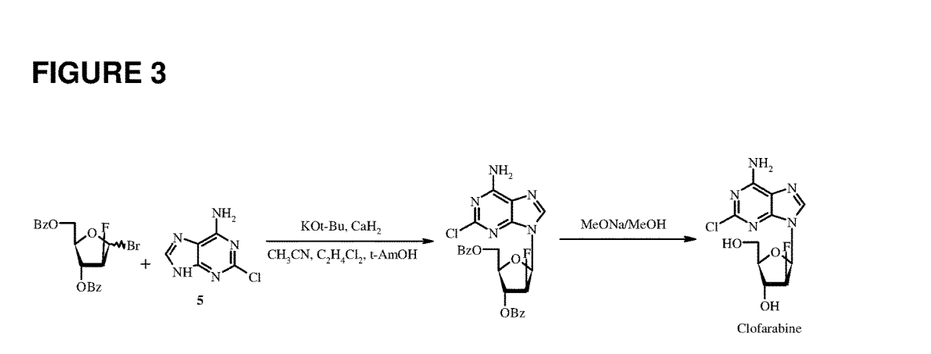
FIG. 3 illustrates the synthesis scheme for the production of clofarabine as disclosed in U.S. Pat. No. 6,680,382.

The further modification of the method of Montgomery and coworkers is disclosed in U.S. Pat. No. 6,680,382 and further illustrated in FIG. 3. This modification involves the use of the potassium salt of 2-chloroadenine 5 obtained by treatment of 2-chloroadenine with t-BuOK instead of the sodium salt of 2,6-dichloropurine, the use of a ternary mixture of solvents (for example, tert-amyl alcohol, CH$_2$Cl$_2$, CH$_3$CN) and addition of CaH$_2$ for the complete removal of water from solvents. The use of low-polarity solvents at the coupling step made it possible to achieve stereoselective proceeding of the reaction (with a ratio of anomer β to α being up to 15:1). In addition, the presence of an amino group in the starting material 2-chloroadenine made it possible to avoid an amination step of the coupling reaction product. As a result, the total yield of purified clofarabine based on fluorinated sugar 4 is about 32%. However, the fluorinated sugar 4 (obtained in four steps from 1-O-acetyl-2,3,5-tri-O-benzoyl-β-D-ribofuranose) is difficult to produce and has a low stability, two still existing disadvantages of this method.

Figure 4:
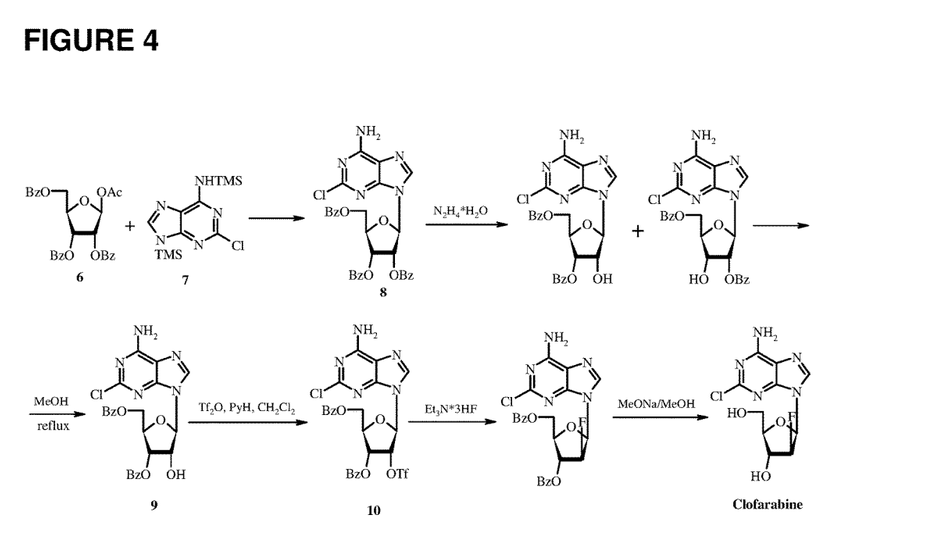
FIG. 4 illustrates the synthesis scheme for the production of clofarabine as disclosed in US patent publication 2012/0010397.

The method disclosed in US patent publication 2012/0010397 relates to the above-referenced second group of methods for preparing clofarabine. It is illustrated in FIG. 4. 2',3',5'-Tri-O-benzoyl-2-chloroadenosine 8 is obtained at the first step by coupling sugar 6 and TMS-protected 2-chloroadenine 7. The further debenzoylation with hydrazine hydrate results in the formation of a mixture of 3',5'- and 2',5''-di-O-benzoyl derivatives. After isomerization of 2',5'-di-O-benzoyl derivative into the 3',5'-derivative 9, triflate 10 is obtained by treatment of compound 9 with triflic anhydride. Triflate 10, after its fluorination and deprotection, results in the final product clofarabine. However, the disadvantages of this method are the large number of isomers (which are difficult to separate) being formed at the coupling step between 6 and 7 (β-N9, α-N7, β-N7 isomers), the use of highly toxic hydrazine hydrate, the overall yield of purified clofarabine being only 15%.

Hence, there is still an ongoing need for improved methods for the synthesis of clofarabine that overcome the limitations of the established synthesis schemes. In particular, there is a need for a synthesis scheme that results in high yield of the product and does not involve the formation of undesired stereoisomers.

Accordingly, it is an object of the present invention to provide such method for the production of clofarabine.

SUMMARY OF THE INVENTION

In one aspect, the present invention relates to a method for the production of clofarabine, comprising:
(a) preparing 2-chloroadenosine by enzymatic transglycosylation between 2-chloroadenine and a compound of formula 1, wherein, R$^1$ is purine or pyrimidine base of formula 2 or formula 3, respectively, -continued wherein R² and R³ are independently selected from the group consisting of —H, —NH₂, —OH, and —CH₃; and R⁴ is selected from the group consisting of —H and —CH₃;

(b) partially protecting the hydroxyl groups of 2-chloroadenosine to obtain a mixture of a compound of formula 4 and a compound of formula 5, wherein R⁵ is independently a hydroxyl protecting group;

(c) isomerizing the compound of formula 4 to the compound of formula 5;

(d) preparing a compound of formula 6 from the compound of formula 5, wherein OR⁶ is a leaving group;

(e) fluorinating the compound of formula 6 to a compound of formula 7; and (f) deprotecting the compound of formula 7 to obtain clofarabine.

In preferred embodiments, the transglycosylation in step (a) is performed by using purine nucleoside phosphorylase or a combination of purine nucleoside phosphorylase and uridine phosphorylase.

In further preferred embodiments, the fluorination in step (e) is performed by using a fluorinating agent. Preferably, the fluorinating agent is selected from the group consisting of hydrofluoric acid and a mixture of hydrofluoric acid and an organic Lewis base. Particularly preferably, the organic Lewis base (used admixed to hydrofluoric acid) is an amine.

In yet further preferred embodiments, substituent R¹ is a pyrimidine base representing uridine; and/or substituent R⁵ is a hydroxyl protecting group representing benzoyl; and/or substituent OR⁶ is a leaving group representing trifluoromethanesulfonate.

DETAILED DESCRIPTION OF THE INVENTION

The present invention is based on the unexpected finding that, when starting from 2-chloroadenosine, the performing of a reaction cascade comprising steps of enzymatic transglycosylation, benzoylation, isomerization, sulfonate ester formation (i.e. sulfonylation), fluorination and deprotection results in the high yield production of clofarabine without the concomitant formation of undesired stereoisomers, thus avoiding major disadvantages of established methods and providing a more efficient and less laborious synthesis scheme.

The present invention will be described in the following with respect to particular embodiments and with reference to certain drawings but the invention is to be understood as not limited thereto but only by the appended claims. The drawings described are only schematic and representative and are to be considered non-limiting.

Where the term "comprising" is used in the present description and claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun e.g. "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art.

In one aspect, the present invention relates to a method for the production of clofarabine, comprising:

(a) preparing 2-chloroadenosine by enzymatic transglycosylation between 2-chloroadenine and a compound of formula 1, wherein, $R^1$ is purine or pyrimidine base of formula 2 or formula 3, respectively, wherein $R^2$ and $R^3$ are independently selected from the group consisting of —H, —NH$_2$, —OH, and —CH$_3$; and $R^4$ is selected from the group consisting of —H and —CH$_3$;

(b) partially protecting the hydroxyl groups of 2-chloroadenosine to obtain a mixture of a compound of formula 4 and a compound of formula 5, wherein $R^5$ is independently a hydroxyl protecting group;

(c) isomerizing the compound of formula 4 to the compound of formula 5;

(d) preparing a compound of formula 6 from the compound of formula 5, wherein OR⁶ is a leaving group;
(e) fluorinating the compound of formula 6 to a compound of formula 7; and (f) deprotecting the compound of formula 7 to obtain clofarabine.

Figure 5:
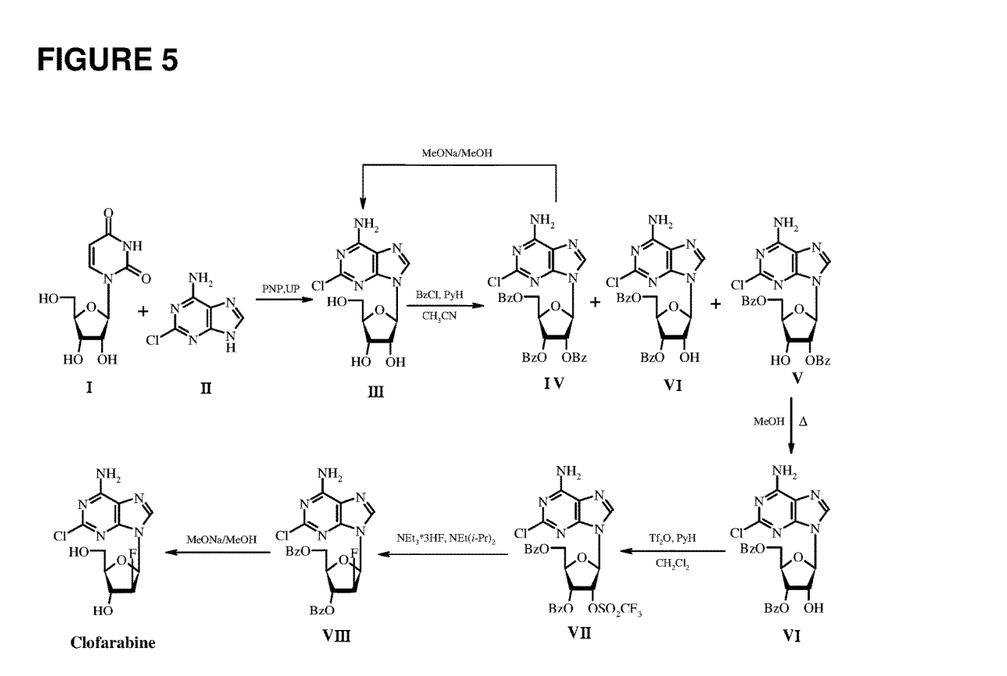
FIG. 5 illustrates the synthesis scheme for the production of clofarabine according to the present invention.

The method according to the present invention is schematically summarized in FIG. 5. In the following, the numbering of the compounds corresponds to the nomenclature used in FIG. 5. 2-Chloroadenosine (III) is obtained by an enzymatic transglycosylation reaction between 2-chloroadenine (II) and any nucleoside which contain ribose, preferably uridine (I) (as it is readily soluble and readily accessible) using enzymes, such as preferably purine nucleoside phosphorylase (PNP) and uridine phosphorylase (UP). This reaction is reversible. To shift the equilibrium toward product (III), an excess of uridine of 1.5 to 5 equivalents, preferably 3.3, is used. The reaction may be conducted at a temperature of 40 to 70° C., preferably at a temperature of 58 to 61° C.

Due to the stereospecificity of enzymatic transglycosylation, the only product of glycosylation is the β-anomer (III). 2-chloroadenosine may be purified from the starting reagents (I), (II) and uracil (by-product), for example, by using low-pressure preparative chromatography. Typically, conditions allowing 2-chloroadenosine to be retained by the sorbent were chosen, while the vast majority of impurities were not retained on the column. It enabled to simplify the purification process, by comprising only "application" and "washing" steps.

The 2-chloroadenosine obtained is then preferably benzoylated with benzoyl chloride in the presence of pyridine. In this reaction, benzoyl chloride may be employed in an amount ranging from 1.8 to 2.5 equivalents, preferably 2.3 equivalents, based on the triol compound of formula (III). The reaction may be conducted at a temperature of −10 to 20° C., preferably at a temperature of 0 to 5° C.

As a by-product, up to 35% of 2',3',5'-tri-O-benzoyl-2-chloroadenosine (IV) may be formed. However, presence of this by-product does not interfere with the subsequent isomerization step and may also easily by separated during crystallization of the 3',5'-di-O-benzoyl derivative. Thus, almost the entire amount of the starting compound 2-chloroadenosine finally results in the formation of the 3',5'-di-O-benzoyl derivative.

Subsequently, an isomerization of the 2',5'-di-O-benzoyl isomer (V) to the 3',5'-di-O-benzoyl isomer (VI) is performed. The migration of the preferred benzoyl group from the 2 to the 3' position in nucleosides established in the art (cf. inter alia Maruyama, T. et al. (1999) *Chem. Pharm. Bull.* 47, 966-970). Preferably, the isomerisation reaction is performed by boiling in methanol for 40-45 hours with vigorous stirring. The resulting crystals obtained after a hot filtration of the reaction mixture have a purity of >98% (HPLC), while almost all impurities remain in the mother liquor, from which 2-chloroadenosine may be isolated after reworking.

Subsequent sulfonylation of the compound of formula VI is performed by treatment with $Tf_2O$ using pyridine as a base. In this reaction, triflic anhydride may be employed in an amount ranging from 1.3 to 2.0 equivalents, preferably 1.6 equivalents, based on the compound of formula (VI). The solvent may be an organic solvent, such as acetonitrile, tetrahydrofuran, dichloromethane, chloroform, preferably dichloromethane. The reaction may be conducted at a temperature of −20 to 30° C., preferably at a temperature −10 to 0° C.

In the next step, the fluoroderivative (VIII) may be obtained by treatment of the triflate (VII) with fluorinating agents, such as $NEt_3*3HF$, TBAF or $TBAF*(t-BuOH)_4$, preferably $NEt_3*3HF$, for example by using diisopropylethylamine as a base. The solvent may be, for example, ethyl acetate, tetrachloromethane, toluene, acetonitrile, preferably toluene. The reaction may be conducted at a temperature of 0 to 100° C., preferably at a temperature of 35 to 40° C. The protected clofarabine obtained may be crystallized from a mixture of ethyl acetate and methanol. Under the above conditions, the yield of the reaction product after crystallization is about 60%.

Finally, the protected clofarabine is deprotected under mild conditions. These mild conditions (30 min at 30° C.) make it possible to carry out the reaction without any side reactions. Methylbenzoate formed is separated by extraction with methylene chloride, and clofarabine, contained in the aqueous phase, is purified using low-pressure preparative chromatography followed by crystallization. The clofarabine obtained has a high purity without detectable amounts of impurities. The overall yield of clofarabine is about 30-40%.

The invention is further described by the figures and the following examples, which are solely for the purpose of illustrating specific embodiments of this invention, and are not to be construed as limiting the claimed subject matter in any way.

EXAMPLES

Example 1a

Preparation of 2-chloroadenosine (III) from 2-chloroadenine and uridine 400 g of uridine and 150 g of $KH_2PO_4$ were dissolved with stirring in a mixture of water (52 l) and DMSO (1.8 l) at 58-61° C. To the resulting solution, a first portion (0.75 l) of a solution prepared from 2-chloroadenine (85 g), water (7 l), and KOH (120 g) was added. The pH of the resulting mixture was adjusted to 7.1-7.2 with aqueous KOH solution. Solutions of uridine phosphorylase and purine nucleoside phosphorylase were added with stirring at 58-61° C. The remaining second portion of the 2-chloroadenine solution was successively added with stirring over a period of 3 hours to the reaction mixture at 58-61° C. keeping pH in the range of 7.1-7.2 with aqueous HCl solution. Afterwards, the reaction mixture was stirred for 1 hour at 58-61° C., and NaOH was added in order to adjust the pH 11.

The resulting solution containing 2-chloroadenosine was purified by means of preparative chromatography, followed by isolation of the product involving crystallization in water, yielding 120 g of the title compound. The typical purity of 2-chloroadenosine was >99%, and the yield on the basis of 2-chloroadenine was >85%.

Example 1b

Preparation of 2-chloroadenosine (III) from 2-chloroadenine and guanosine 229 g of guanosine and 75 g of $KH_2PO_4$ were dissolved with stirring in a mixture of water (52 l) and DMSO (1.8 l) at 58-61° C. To the resulting solution, a first portion (0.75 l) of a solution prepared from 2-chloroadenine (42 g), water (7 l), and KOH (60 g) was added. The pH of the resulting mixture was adjusted to 7.1-7.2 with aqueous KOH solution. A solution of purine nucleoside phosphorylase was added with stirring to the reaction mixture at 58-61° C. The remaining second portion of the 2-chloroadenine solution was successively added with stirring over a period of 3 hours to the reaction mixture at 58-61° C. keeping pH in the range of 7.1-7.2 with aqueous HCl solution. Afterwards, the reaction mixture was stirred for 1 hour at 58-61° C., and NaOH was added in order to adjust the pH 11.

The resulting solution containing 2-chloroadenosine was purified by means of low-pressure reverse phase column chromatography, followed by isolation of the product involving crystallization in water, yielding 53 g of the title compound. The typical purity of 2-chloroadenosine was >99%, and the yield on the basis of 2-chloroadenine was >70%.

Example 2

Benzoylation of 2-chloroadenosine

A solution of 2-chloroadenosine (750 g) in pyridine (7.5 l) was cooled down to −5-0° C. Afterwards, a solution of benzoyl chloride (720 g) in acetonitrile (1440 ml) was slowly added to the reaction mixture with stirring and cooling. Thereby, the internal temperature of the reaction mixture should not be higher than 5° C. The mixture was incubated for 30 min under the same conditions. Thereafter, the solvents were evaporated under reduced pressure at a temperature of 60° C. The residue was dissolved in $CH_2Cl_2$. and successively washed with 1M aqueous $H_2SO_4$ solution, saturated aqueous $NaHCO_3$ solution, and water. The organic phase was evaporated under reduced pressure to obtain a mixture of 2-chloro-9-(2',5'-di-O-benzoyl-β-D-ribofuranosyl)-adenine and 2-chloro-9-(3',5'-di-O-benzoyl-β-D-ribofuranosyl)-adenine (both together about 65% in total by HPLC), as well as 2',3',5'-tri-O-benzoyl-2-chloroadenosine (about 30% by HPLC).

Example 3

Isomerization of 2-chloro-9-(2',5'-di-O-benzoyl-β-D-ribofuranosyl)-adenine (V) to 2-chloro-9-(3',5'-di-O-benzoyl-β-D-ribofuranosyl)-adenine (VI)

The mixture of 2-chloro-9-(2',5'-di-O-benzoyl-β-D-ribofuranosyl)-adenine and 2',3',5'-tri-O-benzoyl-2-chloroadenosine as prepared in Example 2 was added to 25 l of MeOH. The resulting mixture was refluxed for 40-45 hours with vigorous stirring. Afterwards, the mixture was hot-filtrated under vacuum, and the filter cake washed with MeOH. The filtrate containing 2',3',5'-tri-O-benzoyl-2-chloroadenosine and 2-chloro-9-(2',5'-di-O-benzoyl-β-D-ribofuranosyl)-adenine was directed to reworking in order to obtain 2-chloroadenosine by hydrolysis. The solid was dried in vacuum at 50° C. to obtain 880 g of 2-chloro-9-(3',5'-di-O-benzoyl-β-D-ribofuranosyl)-adenine with an HPLC purity of >98%.

Example 4

Preparation of 2-chloro-9-(3',5'-di-O-benzoyl-2'-O-trifluoromethylsulfonyl-β-D-ribofuranosyl)-adenine (VII)

2-Chloro-9-(3',5'-di-O-benzoyl-β-D-ribofuranosyl)-adenine (880 g) was suspended in a mixture of pyridine (0.8 l) and $CH_2Cl_2$ (8 l). Under $N_2$ atmosphere, the solution of triflic anhydride (455 ml) in $CH_2Cl_2$ (1500 ml) was slowly added to the reaction mixture with stirring and cooling at −10-0° C. The reaction mixture was incubated for 30 min under the same conditions. Then, saturated aqueous $NaHCO_3$ solution was added with stirring until the pH of the resulting mixture was adjusted to 7. The organic phase was separated, washed with water, and evaporated under reduced pressure to yield 1000 g (95% yield) of the title product, having an HPLC purity of >95%.

Example 5

Preparation of 2-chloro-9-(3',5'-di-O-benzoyl-2'-deoxy-2'-fluoro-β-D-arabinofuranosyl)-adenine (VIII)

2-Chloro-9-(3',5'-di-0-benzoyl-2'-O-trifluoromethylsulfonyl-β-D-ribofuranosyl)-adenine as prepared in example 4 was suspended in 5 l of toluene. N,N-Diisopropylethylamine (350 ml) and triethylamine trihydrofluoride (1.2 l) were successively added with stirring. The reaction mixture was stirred for 48 hours at 35-40° C. and evaporated under reduced pressure. The residue was treated with ethyl acetate and filtered. Saturated aqueous $NaHCO_3$ solution was added to the filtrate with stirring until the pH of the resulting mixture was adjusted to 7. The organic phase was separated, washed with water, and evaporated under reduced pressure. The residue was dissolved in methanol (1.5 l) while stirring at 60° C. The solution obtained was kept at 2-6° C. for 2-3 hours until full precipitation. The precipitate formed was filtered, washed with methanol and dried to yield 540 g (60% yield) of the title product, having an HPLC purity of >95%.

Example 6

Preparation of 2-chloro-9-(2'-deoxy-2'-fluoro-β-D-arabinofuranosyl)-adenine (i.e. clofarabine)

2-Chloro-9-(3',5'-di-O-benzoyl-2'-deoxy-2'-fluoro-β-D-arabinofuranosyl)-adenine as prepared in Example 5 was suspended in 1.5 l of methanol. 30 ml of 10% methanolic MeONa solution was added and the reaction mixture stirred for 30 min at 30° C. Afterwards, water (1.5 l) and $CH_2Cl_2$ (1.5 l) were added to the reaction mixture. After stirring for 10 min the aqueous phase was separated and evaporated under reduced pressure down to a volume of approximately 1.5 l. The resulting solution containing clofarabine was purified by means of low-pressure preparative column chromatography, followed by isolation of the product involving crystallization in a water/acetone mixture, yielding 260 g of the title compound. The typical purity of clofarabine was >99.9%, and the overall yield (after 6 steps) was 32%.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. Method for the production of clofarabine, comprising:
   (a) preparing 2-chloroadenosine by enzymatic transglycosylation between 2-chloroadenine and a compound of formula 1,

1 wherein, $R^1$ is purine or pyrimidine base of formula 2 or formula 3, respectively,

2

3 wherein $R^2$ and $R^3$ are independently selected from the group consisting of —H, —NH$_2$, —OH, and —CH$_3$; and $R^4$ is selected from the group consisting of —H and —CH$_3$;

(b) partially protecting the hydroxyl groups of 2-chloroadenosine to obtain a mixture of a compound of formula 4 and a compound of formula 5,

4

5 wherein $R^5$ is independently a hydroxyl protecting group;

(c) isomerizing the compound of formula 4 to the compound of formula 5;

(d) preparing a compound of formula 6 from the compound of formula 5,

6 wherein $OR^6$ is a leaving group;

(e) fluorinating the compound of formula 6 to a compound of formula 7; and (f) deprotecting the compound of formula 7 to obtain clofarabine.

2. The method of claim 1, wherein the transglycosylation in step (a) is performed by using purine nucleoside phosphorylase or a combination of purine nucleoside phosphorylase and uridine phosphorylase.

3. The method of claim 1, wherein the fluorination in step (e) is performed by using a fluorinating agent.

4. The method of claim 3, wherein the fluorinating agent is selected from the group consisting of hydrofluoric acid and a mixture of hydrofluoric acid and an organic Lewis base.

5. The method of claim 4, wherein the organic Lewis base is an amine.

6. The method of claim 1, wherein $R^1$ is a pyrimidine base representing uridine.

7. The method of claim 1, wherein $R^5$ is a hydroxyl protecting group representing benzoyl.

8. The method of claim 1, wherein $OR^6$ is a leaving group representing trifluoromethanesulfonate.

* * * * *